United States Patent [19]

Baker

[11] 3,979,507

[45] Sept. 7, 1976

[54] DIAGNOSTIC SYSTEM FOR ORGAN ABNORMALITIES

[75] Inventor: Albert Leroy Baker, Matteson, Ill.

[73] Assignee: Wilson Pharmaceutical & Chemical Corporation, Chicago, Ill.

[22] Filed: Nov. 23, 1973

[21] Appl. No.: 418,618

[52] U.S. Cl. ............................. 424/1.5; 23/230 B; 424/12
[51] Int. Cl.² ................ A61K 43/00; A61K 39/00; G01T 1/16
[58] Field of Search ................... 424/1, 12; 23/230 B

[56] References Cited

UNITED STATES PATENTS

| 3,171,783 | 3/1965 | Fisk | 424/12 |
| 3,704,282 | 11/1972 | Spector | 424/12 X |
| 3,766,162 | 10/1973 | Spector | 424/12 X |

OTHER PUBLICATIONS

Smith et al., Clin. Exp. Immunol., vol. 13, Feb., 1973, pp. 209–212.
Espinosa, Lab. Investigation, vol. 29, No. 5, Nov., 1973, pp. 556–561.
Aner et al., Int Arihs Alleigy Appl. Imunol, vol. 42, 1972, pp. 871–884.
Beloshapkina et al., Nature (Lond.), vol. 214, 1967, pp. 1366–1368.
Dorner et al., Fed. Proc. 21; 1962, p. 824.
Espinosa, Fed. Proc. 32, 1973, p. 824.
Espinosa et al., Proc. Soc. Exp. Biol. Med., vol. 111, 1962, pp. 174–177.
Espinosa et al., J. Immunol., vol. 100, 1968, pp. 1020–1031.
Espinosa et al., J. Immunol., vol. 105, 1970, pp. 416–425.
Hirayania et al., Nature (Lond.), vol. 212, 1966, pp. 1061–1062.
Meyer zum Büshenfelde et al., Clin. Exp. Inmunol., vol. 91, 1965, pp. 89–102.
Milgrom et al., J. Immunol., vol. 91, 1965, pp. 157–163.
Schumacher et al., Klin. Wochenschv., vol. 47, 1969, pp. 806–810.
Espinosa et al., J. Immunol., vol. 106, 1971, pp. 611–618.

Primary Examiner—Leland A. Sebastian
Assistant Examiner—Christine M. Nucker
Attorney, Agent, or Firm—Dressler, Goldsmith, Clement, Gordon & Shore, Ltd.

[57] ABSTRACT

A system is provided for the detection and identification of a diseased or impaired organ in a patient through detection and measurement in the patient's blood, or other body fluid specimen, of an antigen which is normally present in healthy organs of the same kind and normally not present in the blood of a healthy person. The system includes a method for producing and purifying an antibody to the antigen, and for utilizing the antibody to detect and measure an antigen in the patient's blood.

12 Claims, No Drawings

DIAGNOSTIC SYSTEM FOR ORGAN ABNORMALITIES

BACKGROUND OF THE INVENTION

This invention relates to the detection and identification of a diseased or impaired organ in a human patient. The desirability of a laboratory test as an aid to pinpointing the nature of an ailment has been long recognized because of the facts that (1) different disease conditions may manifest similar symptoms, and (2) the same disease condition may produce different symptoms in different patients.

It has been observed by prior workers in the field that certain disease conditions in certain organs of the body, such as the heart, liver, kidney, skeletal muscle, or lung, produce abnormal substances in the blood of the patient and diagnostic systems have been proposed which are based on the detection of these abnormal substances where they are present. Diagnostic systems are also in use in which materials normally present in the blood of a healthy human being are detected and measured in the blood of a patient to ascertain whether any of these materials is present in the patient's blood in an abnormal amount.

The present invention is based upon a different principle and upon the discovery that in certain abnormal conditions in a human organ there is a "spilling over" into the bloodstream of substances which are present in that organ when it is in a normal, healthy condition but which are not ordinarily present in substantial concentrations in the blood of a healthy human being.

Summary of the Invention

In accordance with one aspect of the instant invention a diagnostic material is provided comprising antibodies to at least one antigen normally present in the tissue of healthy specimens of a particular human organ and substantially free of any antibodies to all antigens normally present in the blood of a healthy human being.

In accordance with another aspect of the invention, a diagnostic method is provided in which there is added to the blood serum or plasma of a patient, or to a fraction thereof, an antiserum fraction derived from a host animal which contains at least one antibody to an antigen which is found in healthy specimens of a particular human organ and which is substantially absent in normal human blood but present in human blood when said organ is in a damaged or diseased condition, and thereafter determining the amount or the presence, if any, of antigen-antibody complex in said extract resulting from said addition.

Specifically, this invention involves the preparation of an extract fraction from the tissue of one or more normal, healthy human hearts, livers, kidneys, or other specific organs, the injection of the fraction into a host animal, such as a rabbit or a goat, to enable the host animal to develop antibodies to the antigens in the fraction, the drawing of blood from the host animal, and the separation from said blood of antibodies to antigens found in normal human blood to leave a blood fraction containing antibodies to antigens contained in the human organ but substantially free of antibodies to antigens contained in the blood of normal, healthy human beings and preferably also free of antibodies to antigens contained in other organs.

The system of this invention is applicable to the detection of diseased or abnormal conditions in any one of a number of organs which have distinctive tissue characteristics. The system may be utilized for example, with tissue derived from normal human heart, liver, kidney, skeletal muscle, bone, prostate, intestine, breast tissue, lymph nodes, lung, stomach, brain or nerves.

In a typical preparation, tissue from normal human livers, for example, is minced and ground and treated to produce an aqueous extract and then fractionated to isolate an antigen fraction which is immunogenic.

The immunogenic antigen fraction is injected into a host animal, such as a rabbit or a goat, to produce antibodies to the liver antigen fraction and an antiserum is then isolated from the blood of the host animal. The antiserum is purified by removal of unwanted antibodies, such as antibodies to antigens normally found in human blood and can then be used to test for the presence of liver antigen in the blood of a patient.

EXAMPLE 1

PREPARATION OF AN ANTIGEN FRACTION FROM NORMAL HUMAN LIVER AND OF SPECIFIC HOMOLOGOUS ANTISERA IN RABBITS

A. Preparation of Antigen Fractions

1. Liver tissue, obtained at autopsy and frozen, was thawed, trimmed, and cut into small pieces. The minced tissue was ground in a Waring Blender with 3 volumes 0.05 M tris-acetate (trishydroxymethyl aminomethane), pH 8.0, containing 0.1 M NaCl, for 2 minutes. The resulting suspension was stirred 1.5 hours at 4°C.

2. The above suspension was centrifuged 30 minutes at 15,000 X g. The supernatant was decanted through 4 layers of cheesecloth.

3. Following dialysis against two changes of 16 liters of cold deionized water, the suspension was centrifuged 30 minutes at 15,000 X g. The supernatant was decanted, frozen, and lyophilized.

4. 2.0 g of the above-lyophilized human liver extract was suspended in 20 ml of 0.095 M tris-acetate, $pH$ 7.5, containing 0.15 M NaCl, and centrifuged 20 minutes at 23,000 X g.

5. The clarified solution was applied to a 2.6 X 84.7 cm column of Sephadex G-200, equilibrated in and eluted with 0.095 M tris-acetate, 0.15 M NaCl, $pH$ 7.5. The flow rate was maintained at 30 ml/hour; fractions of 5 ml were collected. Sephadex G-200 is a gel filtration material which is one of a family of hydrophilic water-insoluble cross-linked dextran polymer gels which are commercially available under the name "Sephadex" from A B Pharmacia, Uppsala, Sweden, and which are described in British Patent No. 854,715. Sephadex G-200 has an approximate molecular weight exclusion limit of 200,000, a water regain (g.$H_2O$/g. dry gel) of 20.0 ± 2.0, a particle size of 40–120 microns and a bed volume (ml./g. of dry gel) of 30–40.

6. The fractions obtained in step 5 were monitored by absorbance at 280 nm and immunodiffusion (in 2% agarose, 7.5% glycine, 1% NaCl, 0.1% $NaN_3$, pH 7.1) with adsorbed anti-liver C sera (prepared as described below in Section B).

7. Two pools of fractions, designated fractions $C_1$ and $C_2$, in order of appearance in the eluate, were made based on positive precipitin reactions with the adsorbed anti-liver C sera.

8. The pools $C_1$ and $C_2$ were concentrated separately approximately five fold by ultrafiltration (Amicon ultrafiltration cell, employing a PM 30 membrane having a molecular weight cut-off of about 30,000 daltons.

9. The concentrates were individually dialyzed against 0.1 M tris-acetate, pH 8.0, and clarified by centrifugation at 23,000 × g for 30 minutes.

10. The resulting solutions were applied to respective columns (approximately 2.5 × 50 cm) of QAE-Sephadex A-50. The columns were equilibrated in 0.1 M tris-acetate, pH 8.0. Elution was accomplished with a linear gradient from 500 ml 0.1 M trisacetate, pH 8.0, to 500 ml 0.1 M tris-acetate, 1.0 M NaCl, pH 8.0. A flow rate of 30 ml/hour was maintained and 10 ml fractions were collected. QAE-Sephadex A-50 is an anion exchange material which is a quaternary aminoethyl derivative of Sephadex (described above).

11. Fractions were monitored as indicated in Step No. 6 above.

12. Respective pools of fractions (eluting from approximately 0.5 to 0.7 M NaCl) were made based on positive precipitin reactions with the adsorbed anti-liver C sera.

13. Antigen fractions $C_1$ and $C_2$ from the QAE-Sephadex columns were separately concentrated approximately twenty-fold as indicated Step No. 8 above.

14a. In order to remove normal human serum components, concentrated antigen fraction $C_1$ from Step No. 13 was applied to a column (1.5 × 73 cm) of the globulin fraction of rabbit anti-serum to normal human serum, immobilized on Sepharose 4B. Sepharose 4B is one of a family of agarose gels commercially available from A B Pharmacia, Uppsala, Sweden, under the name "Sepharose." The gels are available as aqueous suspensions in 0.02 percent sodium azide as preservative. The gels are prepared in beaded form having a selected particle size and percent agarose. The concentration of the agarose in the gel determines its fractionation range. Sepharose 4B has a particle size of from 40 to 190 microns and contains 4 percent by weight agarose. It has a fractionation range which separates materials of molecular weight greater than 100,000. The column packing had been prepared as follows:

100 ml of Sepharose 4B, which had been extensively washed with water, was suspended in 100 ml 0.1 M $Na_2CO_3$, pH 11.0, and placed in an icebath. 12 g solid CNBr were added to the Sepharose 4B with stirring. The pH was monitored and maintained at 11.0 with the addition of 6 M NaOH for 45 minutes. The Sepharose was filtered on a Buchner funnel and washed exhaustively with 0.5 M $NaHCO_3$, pH 9.0, and added to a solution of the rabbit gamma globulin fraction (from 10 ml of rabbit anti-human serum) in the same buffer. Stirring was maintained overnight at room temperature. The Sepharose-globulin conjugate was filtered on a Buchner funnel and washed exhaustively with water and suspended in 100 ml of 0.1 M glycine in 0.5 M $Na_2HPO_4$, pH 9.0, and stirred 3 hours. The Sepharose-globulin conjugate was filtered and washed extensively with 0.1 M $Na_2HPO_4$, pH 8.0; washed extensively with water; suspended in 0.095 M tris-acetate, 0.15 M NaCl, pH 7.5, and packed into the column.

The column was eluted with 0.095 M tris-acetate, 0.15 M NaCl, pH 7.5, at a flow rate of 18 ml/hour. Five ml fractions were collected.

14b. In order to further purify antigen fraction $C_2$, the concentrate from Step No. 13 was applied to a 2.5 × 70 cm column of Sephadex G-200, equilibrated in and eluted with 0.095 M trisacetate, 0.15 M NaCl, pH 7.5. The flow rate was maintained at 30 ml/hour; fractions of 10 ml were collected. The fractions were monitored as indicated in Step No. 6 above. A pool of fractions reacting positively with the adsorbed anti-liver C sera was made and concentrated as in Step No. 8 above. The concentrated antigen fraction $C_2$ was then subjected to chromatography on a column of immobilized globulin fraction of rabbit antiserum to normal human serum as described in Step No. 14a above.

15. The fractions containing the antigen fractions $C_1$ and $C_2$ from Steps No. 14a and 14b were monitored as indicated in Step No. 6 above.

16. Respective pools of antigen fractions $C_1$ and $C_2$ were made based on positive precipitin reactions with the adsorbed anti-liver C sera.

17. Concentration of both pools was effected as indicated in Step No. 8 above.

18. The final solutions were stored frozen until use.

B. Preparation of Purified Antisera

1. New Zealand white rabbits were injected intramuscularly with 2.0 absorbance units (at 280 nm) of liver antigen C ($C_1 + C_2$) fraction. Initial injections were given in Complete Freund's Adjuvant. Boosters were given monthly or biweekly thereafter in Incomplete Freund's Adjuvant.

2. Bleedings were taken from ear veins between 7 and 14 days following an injection of antigen; the serum was obtained following clotting and preliminarily assessed as follows: To 100λ aliquots of each serum was added 30% (v/v) normal human plasma containing 50 mg/ml normal human kidney extract. Following incubation for 2 hours at room temperature, adsorbed serum was tested by immunodiffusion (in 2% agarose, 7.5% glycine, 1% NaCl, 0.1% $NaN_3$, pH 7.1) against normal human liver extract, heart extract, skeletal muscle extract, kidney extract, and plasma. All tissue extracts were 5 mg/ml in saline. Specific antibody as asertained under these conditions, appeared within two months after beginning the immunization schedule.

3. Pooling of antisera from four rabbits exhibiting specific antibody as indicated in Step No. 2 was effected over a 1-month period and totaled 226 ml.

4. 226 ml of saturated $(NH_4)_2SO_4$ was added dropwise to the serum pool with stirring over a 15-minute period at 4°C. The suspension was stirred an additional hour. The gamma globulin containing precipitate was collected by centrifugation at 15,000 × g for 20 minutes.

5. The precipitate was dissolved in 50 ml of 0.095 M trisacetate, 0.15 M NaCl, pH 7.5 and dialyzed against 1 liter of the buffer overnight. The dialyzed solution was clarified by centrifugation at 23,000 × g for 30 minutes.

6. The solution was applied to a 5.0 × 80 cm column of Sephadex G-200, equilibrated in and eluted with 0.095 M trisacetate, 0.15 M NaCl, ph 7.5. A flow rate of 60 ml/hour was maintained and 6 ml fractions were collected.

7. The fractions were monitored by absorbance at 280 nm and by immunodiffusion (in 2% agarose, 7.5% glycine, 1.0% NaCl, 0.1% $NaN_3$, pH 7.1) with 5 mg/ml human liver extract in saline.

8. Fractions with positive precipitin reactions with liver extract were pooled and concentrated by ultrafiltration as indicated in Step No. A-8 above.

9. Antibodies against normal human plasma were removed from the concentrated solution by passage over a column (2.5 × 80 cm) of normal human plasma immobilized on Sepharose 4B. The column contained 0.093 ml of plasma per ml of Sepharose, and was prepared by the procedures cited in Step No. A-14a above. The column was equilibrated in and eluted with 0.095 M tris-acetate, 0.15 M NaCl, pH 7.5. Flow rate was maintained at 12 ml/hour and 6 ml fractions were collected.

10. The fractions were monitored as indicated in Step No. B-7 above.

11. Fractions with positive precipitin reactions with liver extract were pooled and concentrated as indicated in Step No. A-8 above.

12. The purified, concentrated antiserum was stored frozen or refrigerated until use.

EXAMPLE 2

Preparation of an Antigen Fraction from Normal Human Kidney and of Specific Homologous Antisera in Rabbits A. Preparation of Antigen Fraction 1. Normal kidney tissue, obtained at autopsy and frozen, was thawed, trimmed, and cut into small pieces. The minced tissue was ground in a Waring Blender with 3 volumes 0.05 M tris-acetate, pH 8.0, containing 0.1 M NaCl, for 1 minute. The resulting suspension was stirred one hour at 4°C.

2. The above suspension was centrifuged 30 minutes at 15,000 × g. The supernatant was decanted through 4 layers of cheesecloth.

3. Following dialysis against two changes of 16 liters of cold deionized water, the suspension was frozen and lyophilized.

4. 1.1 g of the above lyophilized human kidney extract was suspended in 20 ml of 0.095 M tris-acetate, pH 7.5, containing 0.15 M NaCl, and centrifuged 20 minutes at 16,000 × g.

5. The clarified solution was applied to a 2.5 × 77 cm column of Sephadex G-200, equilibrated in and eluted with 0.095 M tris-acetate, 0.15 M NaCl, pH 7.5. The flow rate was maintained at 28 ml/hour; fractions of 4.6 ml were collected.

6. The fractions were monitored by absorbance at 280 nm and immunodiffusion (in 2% agarose, 7.5% glycine, 1% NaCl, 0.1% $NaN_3$, pH 7.1) with adsorbed anti-kidney A sera (prepared as described below in Section B).

7. A pool of fractions, designated kidney antigen A, was made based on positive precipitin reactions with the adsorbed anti-kidney A sera.

8. The pool was concentrated approximately five-fold by ultrafiltration (Amicon ultrafiltration cell, employing a PM 10 membrane having a molecular weight cut-off of about 10,000 daltons.

9. The concentrate was dialyzed against 0.085 M trisacetate, pH 8.0, and clarified by centrifugation at 23,000 × g for 30 minutes.

10. The resulting solutions were applied to a column (approximately 2.5 × 50 cm) of QAE-Sephadex A-50. The column was equilibrated in 0.095 M tris-acetate, pH 8.0. Elution was initiated with 0.095 M tris-acetate, pH 8.0. After 240 ml of effluent had been collected, elution was continued with a linear gradient from 500 ml 0.095 M tris-acetate, pH 8.0, to 500 ml 0.1 M tris-acetate, 1.0 M NaCl, pH 8.0. A flow rate of 20 ml/hour was maintained and 5 ml fractions were collected.

11. Fractions were monitored as indicated in Step No. 6 above.

12. Four separate pools of fractions were made based on positive precipitin reactions with the adsorbed anti-kidney A sera.

13. Kidney antigen fraction A, eluted first from the QAE-Sephadex column, was concentrated approximately ten-fold as indicated in Step No. 8 above.

14. In order to further purify kidney antigen fraction A, the concentrate from Step No. 13 was applied to a 1.5 × 80 cm column of Sephadex G-100, equilibrated in and eluted with 0.095 M tris-acetate, 0.15 M NaCl, pH 7.5. The flow rate was maintained at 42 ml/hour; fractions of 4 ml were collected. Sephadex G-100 is one of the "Sephadex" family of cross-linked dextran polymer gels, described above. The "G-100" species has an approximate molecular weight exclusion limit of 100,000, a water regain (g. $H_2O$/g. dry gel) of 10.0 ± 1.0, a particle size of 40–120 microns and a bed volume (ml./g. of dry gel) of 15–20.

15. Fractions were monitored as indicated in Step No. 6 above.

16. The pool of kidney antigen fraction, designated A, was made based on positive precipitin reactions with the adsorbed anti-kidney A sera.

17. The final solution was stored frozen until use.

B. Preparation of Purified Antisera

1. New Zealand white rabbits were injected intramuscularly with 3.0 absorbance units (at 280 nm) of kidney antigen A (Step No. 8 above). Initial injections were given in Complete Freund's Adjuvant. Boosters were given monthly or biweekly thereafter in Incomplete Freund's Adjuvant.

2. Bleedings were taken from ear veins between 7 and 14 days following an injection of antigen; the serum was obtained following clotting and preliminarily assessed as follows:

To 100λ aliquots of each serum was added 20% (v/v) normal human plasma containing 50 mg/ml normal human liver extract. Following incubation for 2 hours at room temperature, adsorbed serum was tested by immunodiffusion in 2% agarose, 7.5% glycine, 1% NaCl, 0.1% $NaN_3$, pH 7.1, against normal human liver extract, heart extract, skeletal muscle extract, kidney extract, and plasma (all tissue extracts at 5 mg/ml in saline). Specific antibody, as ascertained under these conditions, appeared within two months after beginning the immunization schedule.

3. Pooling of antisera from one rabbit exhibiting specific antibody as indicated in Step No. 2 was effected over a 1-month period.

4. 50 ml of serum was applied to a 5.0 × 80 cm column of Sephadex G-200, equilibrated in and eluted with 0.095 M trisacetate, 0.15 M NaCl, pH 7.5. A flow rate of 60 ml/hour was maintained.

5. The fractions were monitored by absorbance at 280 nm and by immunodiffusion (in 2% agarose, 7.5% glycine, 1.0% NaCl, 0.1% $NaN_3$, pH 7.1) with 5 mg/ml human kidney extract in saline.

6. Fractions with positive precipitin reactions with kidney extract were pooled and concentrated by ultrafiltration as indicated in Step No. A-8 above.

7. Antibodies against normal human plasma were removed from an aliquot of concentrated solution by passage over a column (1.0 × 20 cm) of normal human plasma immobilized on Sepharose 4B. The column packing had been prepared as follows:

125 ml of Sepharose 4B, which had been extensively washed with water, was suspended in 125 ml 0.1 M $Na_2CO_3$, pH 11.0, and placed in an icebath. 12.5 g solid CNBr were added to the Sepharose 4B with stirring. The pH was monitored and maintained at 11.0 with the addition of 6M NaOH for 45 minutes. The sepharose was filtered on a Buchner funnel and washed exhaustively with 0.5 M NaHCO$_3$, pH 9.0, and added to 30 ml of normal human plasma which had been diluted to 125 ml in the NaHCO$_3$ buffer. Stirring was maintained overnight at room temperature. The Sepharose-plasma conjugate was filtered on a Buchner funnel and washed exhaustively with water and suspended in 250 ml of 0.1 M glycine in 0.5 M NaHCO$_3$, pH 9.0, and stirred 1 hour. The Sepharose-plasma conjugate was filtered and washed extensively with 0.095 M tris-acetate, 0.1% sodium azide, pH 7.5.

The column was equilibrated in and eluted with 0.095 M tris-acetate, 0.15 M NaCl, pH 7.5. The flow rate was maintained at 20 ml/hour.

8. The fractions were monitored as indicated in Step No. B-5 above.

9. Fractions with positive precipitin reactions with kidney extract were pooled and concentrated as indicated in Step No. A-8 above.

10. Antibodies against normal human liver were removed from the concentrated solution by passage over a column (1.0 × 20 cm) of normal human liver extract immobilized on Sepharose 4B. The column was prepared by the procedures cited in Step No. B-7 above with the substitution of 125 mg of human liver extract for plasma. The column was equilibrated in and eluted with 0.095 M tris-acetate, 0.15 M NaCl, pH 7.5. The flow rate was maintained at 20 ml/hour.

11. The fractions were monitored as indicated in Step No. B-5 above.

12. Fractions with positive precipitin reactions with kidney extract were pooled and concentrated as indicated in Step No. A-8 above.

13. The purified, concentrated antiserum was stored frozen or refrigerated until use.

EXAMPLE 3

Preparation of an Antigen Fraction from Normal Human Muscle and of Specific Homologous Antisera in Rabbits A. Preparation of Antigen Fraction:

1. Normal psoas muscle tissue, obtained at autopsy and frozen, was thawed, trimmed, and cut into small pieces. The minced tissue was ground in a Waring Blender with 10 volumes 0.1 M tris-acetate, pH 7.5, containing 0.1 M NaCl, for 2 minutes. The resulting suspension was stirred 1.5 hours at 4°C.

2. The above suspension was centrifuged 20 minutes at 10,000 × g. The supernatant was decanted through 4 layers of cheesecloth.

3. Following dialysis against 28 liters of cold deionized water, the suspension was frozen and lyophilized.

4. 87 mg of the above lyophilized muscle extract was suspended in 3 ml of 0.1 M tris-acetate, pH 7.5, containing 0.15 M NaCl, and centrifuged 20 minutes at 15,000 × g.

5. The clarified solution was applied to a 2.6 × 77 cm column of Sephadex G-200, equilibrated in and eluted with 0.1 M tris-acetate, 0.15 M NaCl, pH 7.5. The flow rate was maintained at 30 ml/hour; fractions of 5 ml were collected.

6. The fractions were monitored by absorbance at 280 nm and immunodiffusion (in 2% agarose, 7.5% glycine, 1% NaCl, 0.1% NaN$_3$, pH 7.1) with adsorbed anti-muscle G sera (prepared as described in Section B below).

7. A pool of fractions designated muscle fraction G was made based on positive precipitin reactions with the adsorbed anti-muscle G sera.

8. The pool was concentrated approximately fivefold by ultrafiltration (Amicon ultrafiltration cell, employing PM 10 membrane).

9. The concentrate was dialyzed against 0.1 M trisacetate, pH 8.0, and clarified by centrifugation at 23,000 × g for 30 minutes.

10. The resulting solution was applied to a column (2.6 × 85 cm) of QAE-Sephadex A-50. The column was equilibrated in 0.1 M tris-acetate, pH 8.0. Elution was initiated with a linear gradient from 500 ml 0.1 M tris-acetate, pH 8.0, to 500 ml 0.1 M tris-acetate, 0.3 M NaCl, pH 8.0. Buffered 0.5 M and 2.0 M NaCl were used to stepwise elute following completion of the gradient. A flow rate of 15 ml/hour was maintained.

11. Fractions were monitored as indicated in Step No. 6 above.

12. A pool of fractions (eluting from approximately 0.15 to 0.25 M NaCl) was made based on positive precipitin reactions with the adsorbed anti-muscle G sera.

13. Antigen fraction G from the QAE-Sephadex column was concentrated as indicated in Step No. 8 above.

14. The concentrated antigen pool was rechromatographed on QAE-Sephadex by repeating Steps Nos. 9-13 above.

15. In order to further purify antigen fraction G, the concentrate from Step No. 14 was applied to a 1.6 × 80 cm column of Sephadex G-100, equilibrated in and eluted with 0.1 M trisacetate, 0.15 M NaCl, pH 7.5. The flow rate was maintained at 10 ml/hour. The fractions were monitored as indicated in Step No. 6 above. A pool of fractions reacting positively with the adsorbed anti-muscle G sera was made and stored refrigerated or frozen until use.

B. Preparation of Purified Antisera

1. New Zealand white rabbits were injected intramuscularly with 2.0 to 10.0 absorbance units (at 280 nm) of muscle antigen G. Initial injections were given in Complete Freund's Adjuvant. Boosters were given monthly or biweekly thereafter in incomplete Freund's Adjuvant.

2. Bleedings were taken from ear veins between 7 and 14 days following an injection of antigen; the serum was obtained following clotting and preliminarily assessed as follows:

To 100λ aliquots of each serum was added 30% (v/v) normal human plasma containing 50 mg/ml normal human liver extract. Following incubation for 2 hours at room temperature, adsorbed serum was tested by immunodiffusion in 2% agarose, 7.5% glycine, 1% NaCl, 0.1% NaN$_3$, pH 7.1, against normal human liver extract, heart extract, skeletal muscle extract, kidney extract, and plasma (all tissue extracts at 5 mg/ml in saline). Specific antibody, as ascertained under these conditions, appeared within 6 months after beginning the immunization schedule.

3. Pooling of antiserum from a rabbit exhibiting specific antibody as indicated in Step No. 2 was effected over a 2-month period.

4. To a 20 ml aliquot of antiserum was added 20 ml of saturated (NH$_4$)$_2$SO$_4$ dropwise with stirring over a 15-minute period at 4°C. The suspension was stirred an additional hour. The gamma globulin containing precipitate was collected by centrifugation at 15,000 × g for 20 minutes.

5. The precipitate was dissolved in 4 ml of 0.1 M trisacetate, 0.15 M NaCl, pH 7.5 and dialyzed against 1 liter of the buffer overnight. The dialyzed solution was clarified by centrifugation at 23,000 × g for 30 minutes.

6. The solution was applied to a 2.6 × 80 cm column of Sephadex G-200, equilibrated in and eluted with 0.1 M trisacetate, 0.15 M NaCl, pH 7.5. A flow rate of 15 ml/hour was maintained and 3 ml fractions were collected.

7. The fractions were monitored by absorbance at 280 nm and by immunodiffusion (in 2% agarose, 7.5% glycine, 1.0% NaCl, 0.1% NaN$_3$, pH 7.1) with 5 mg/ml human muscle extract in saline.

8. Fractions with positive precipitin reactions with muscle extract were pooled and concentrated by ultrafiltration as indicated in Step No. A-8 above.

9. Antibodies against normal human plasma were removed from a 20 ml aliquot of antiserum by passage over a column (2.5 × 80 cm) of normal human plasma immobilized on Sepharose 4B. The column contained 0.14 ml of plasma per ml of Sepharose, and was prepared as follows:

500 ml of Sepharose 4B, which had been extensively washed with water, was suspended in 500 ml 0.1 M Na$_2$CO$_3$, pH 11.0, and placed in an icebath. 60 g solid CNBr were added to the Sepharose 4B with stirring. The pH was monitored and maintained at 11.0 with the addition of 6 M NaOH for 45 minutes. The Sepharose was filtered on a Buchner funnel and washed exhaustively with 0.5 M NaHCO$_3$, pH 9.0, and added to 120 ml normal human plasma diluted to 500 ml with the buffer. Stirring was maintained overnight at room temperature. The Sepharose-plasma conjugate was filtered on a Buchner funnel and washed exhaustively with water and suspended in 500 ml of 0.1 M glycine in 0.5 M NaHCO$_3$, pH 9.0 and stirred 3 hours. The Sepharose-plasma conjugate was filtered and washed extensively with 0.1 M NaH$_2$PO$_4$, pH 8.0; suspended in 0.1 M tris-acetate 0.15 M NaCl, pH 7.5, and packed into the column. The column was eluted with 0.1 M tris-acetate, 0.15 M NaCl, pH 7.5, at a flow rate of 15 ml/hour. Three ml fractions were collected.

10. The fractions were monitored by latex agglutination, employing antigen G coated — 0.81 micron latex particles in 0.1 M glycine buffer, pH 8.2.

11. Fractions with positive latex agglutination reactions were pooled and stored refrigerated until use.

EXAMPLE 4

Preparation of an Antigen Fraction from Normal Human Heart and of Specific Homologous Antisera in Rabbits A. Preparation of Antigen Fraction 1. Normal heart tissue, obtained at autopsy and frozen, was thawed, trimmed, and cut into small pieces. The minced tissue was ground in a Waring Blender with 3 volumes 0.05 M tris-acetate, pH 8.0, containing 0.1 M NaCl, for 2 minutes. The resulting suspension was stirred 1.5 hours at 4°C.

2. The above suspension was centrifuged 30 minutes at 15,000 × g. The supernatant was decanted through 4 layers of cheesecloth.

3. Following dialysis against two changes of 16 liters of cold deionized water, the suspension was centrifuged 30 minutes at 15,000 × g. The supernatant was decanted, frozen, and lyophilized.

4. 297 mg of the above lyophilized human heart extract was suspended in 10 ml of 0.1 M tris-acetate, pH 7.5, containing 0.15 M NaCl, and centrifuged 20 minutes at 15,000 × g.

5. The clarified solution was applied to a 2.6 × 77 cm column of Sephadex G-200, equilibrated in and eluted with 0.1 M tris-acetate, 0.15 M NaCl, pH 7.5. The flow rate was maintained at 20 ml/hour; fractions of 5 ml were collected.

6. The fractions were monitored by absorbance at 280 nm and immunodiffusion (in 2% agarose, 7.5% glycine, 1% NaCl, 0.1% NaN$_3$, pH 7.1) with adsorbed anti-heart H sera (prepared as described in Section B below).

7. The pool of fractions designated fraction H was made based on positive precipitin reactions with the adsorbed anti-H sera.

8. An aliquot of 20 ml from the above pool was dialyzed against 0.1 M tris-acetate, pH 7.5, and clarified by centrifugation at 15,000 × g for 30 minutes.

9. The resulting solution was applied to a column (2.6 × 50 cm) of QAE-Sephadex A-50. The column was equiligrated in 0.1 M tris-acetate, pH 7.5. Elution was accomplished with a linear gradient from 300 ml 0.1 M tris-acetate, pH 7.5, to 300 ml 0.1 M tris-acetate, 1.0 M NaCl, pH 7.5. A flow rate of 20 ml/hour was maintained and 3 ml fractions were collected.

10. Fractions were monitored as indicated in Step No. 6 above.

11. The pool of fractions (eluting at approximately 0.45 M NaCl) was made based on positive precipitin reactions with the adsorbed anti-H sera.

12. The pool was further purified by rechromatography on QAE-Sephadex by repeating Steps No. 8–11. The final solution was stored refrigerated until use.

B. Preparation of Adsorbed Antisera

1. New Zealand white rabbits were injected intramuscularly with 2.0 to 8.0 absorbance units (at 280 nm) of heart antigen H. Initial injections were given in Complete Freund's Adjuvant. Boosters were given monthly or biweekly thereafter in Freund's Adjuvant.

2. To 100λ aliquots of each serum was added 30% (v/v) normal human plasma containing 50 mg/ml normal human liver extract. Following incubation for 2 hours at room temperature, adsorbed serum was tested by immunodiffusion in 2% agarose, 7.5% glycine, 1% NaCl, 0.1% NaN$_3$, pH 7.1, against normal human liver extract, heart extract, skeletal muscle extract, kidney extract, and plasma (all tissue extracts at 5 mg/ml in saline). Specific antibody, as ascertained under these conditions, appeared within five months after beginning the immunization schedule.

3. Pooling of antisera from a rabbit exhibiting specific antibody as indicated in Step No. 2 was effected over a three-month period.

4. The antisera was stored frozen until use.

EXAMPLE 5

Preparation of an Antigen Fraction from Normal Human Pancreas and of Specific Homologous Antisera in Rabbits A. Preparation of Antigen Fraction 1. Normal pancreas tissue, obtained at autopsy and frozen, was thawed, trimmed, and cut into small pieces. The minced tissue was ground in a Waring Blender with three volumes 0.05 M tris-acetate, pH 8.0, containing 0.1 M NaCl and 0.005 M $CaCl_2$, for 2 minutes. The resulting suspension was stirred one hour at 4°C.

2. Following adjustment of pH from 6.7 to 7.5 with 2.0 M tris, the above suspension was centrifuged 30 minutes at 15,000 × g. The supernatant was decanted through 4 layers of cheesecloth.

3. Following dialysis against 16 liters of cold deionized water, the suspension was centrifuged 30 minutes at 15,000 × g. The supernatant was decanted, frozen, and lyophilized.

4. 1.0 g of the above lyophilized human pancreas extract was suspended in 20 ml of 0.095 M tris-acetate, $pH$ 7.5, containing 0.15 M NaCl and 0.03 M diisopropylfluorophosphate, and centrifuged 30 minutes at 23,000 × g.

5. The clarified solution was applied to a 2.5 × 71 cm column of Sephadex G-200, equilibrated in and eluted with 0.095 M tris-acetate, 0.15 M NaCl, $pH$ 7.5. The flow rate was maintained at 18 ml/hour; fractions of 9 ml were collected.

6. The fractions were monitored by absorbance at 280 nm and immunodiffusion (in 2% agarose, 7.5% glycine, 1% NaCl, 0.1% $NaN_3$, $pH$ 7.1) with adsorbed anti-pancreas A sera (prepared as described in Section B below).

7. Two pools of fractions, designated fraction $A_1$ and $A_2$, in order of appearance in the eluate, were made based on positive precipitin reactions with the adsorbed anti-pancreas A sera.

8. The pools $A_1$ and $A_2$ were concentrated separately approximately six-fold by ultrafiltration (Amicon ultrafiltration cell, employing PM 30 membrane).

9. The concentrates were individually dialyzed against 0.1 M tris-acetate, $pH$ 8.0, and clarified by centrifugation at 23,000 × g for 30 minutes.

10. The resulting solutions were applied to respective columns (approximately 2.5 × 50 cm) of QAE-Sephadex A-50. The columns were equilibrated in 0.1 M tris-acetate, $pH$ 8.0. Elution was accomplished with a linear gradient from 500 ml 0.1 M tris-acetate, $pH$ 8.0, to 500 ml 0.1 M tris-acetate, 1.0 M NaCl, $pH$ 8.0. A flow rate of 30 ml/hour was maintained and 10 ml fractions were collected.

11. Fractions were monitored as indicated in Step No. 6 above.

12. Respective pools of fractions were made based on positive precipitin reactions with the adsorbed anti-pancreas A sera. Two areas of positive precipitin reactions, designated $A_{1a}$ and $A_{1b}$, were separated upon chromatography of fraction $A_1$.

13. Antigen fractions $A_{1a}$, $A_{1b}$, and $A_2$ from the QAE-Sephadex columns were stored frozen or refrigerated until use.

B. Preparation of Purified Antisera

1. New Zealand white rabbits were injected intramuscularly with 3.0 – 5.0 absorbance units (at 280 nm) of pancreas fraction A (principally fraction $A_2$ from Step No. A-7). Initial injections were given in Complete Freund's Adjuvant. Boosters were given monthly or biweekly thereafter in Incomplete Freund's Adjuvant.

2. Bleedings were taken from ear veins between 7 and 14 days following an injection of antigen; the serum was obtained following clotting and preliminarily assessed as follows:

To 100λ aliquots of each serum was added 20% (v/v) normal human plasma containing 50 mg/ml normal human liver extract. Following incubation for 2 hours at room temperature, adsorbed serum was tested by immunodiffusion in 2% agarose, 7.5% glycine, 1% NaCl, 0.1% $NaN_3$, $pH$ 7.1, against normal human pancreas extract, heart extract, liver extract, kidney extract, and plasma (all tissue extracts at 5 mg/ml in saline). Specific antibody, as ascertained under these conditions, appeared within two months after beginning the immunization schedule.

3. Pooling of antisera from five rabbits exhibiting specific antibody as indicated in Step No. 2 was effected over a 1-month period and totaled 76 ml.

4. 76 ml of saturated $(NH_4)_2SO_4$ was added dropwise to the serum pool with stirring over a 15-minute period at 4°C. The suspension was stirred an additional hour. The gamma globulin containing precipitate was collected by centrifugation at 15,000 × g for 20 minutes.

5. The precipitate was dissolved in 14 ml of 0.095 M trisacetate, 0.15 M NaCl, $pH$ 7.5 and dialyzed against 500 ml of the buffer overnight. The dialyzed solution was clarified by centrifugation at 23,000 × g for 30 minutes.

6. The solution was applied to a 2.5 × 71 cm column of Sephadex G-200, equilibrated in and eluted with 0.095 M trisacetate, 0.15 M NaCl, $pH$ 7.5. A flow rate of 30 ml/hour was maintained and 5 ml fractions were collected.

7. The fractions were monitored by absorbance at 280 nm and by immunodiffusion (in 2% agarose, 7.5% glycine, 1.0% NaCl, 0.1% $NaN_3$, $pH$ 7.1) with 5 mg/ml human pancreas extract in saline containing diisopropylfluorophosphate.

8. Fractions with positive precipitin reactions with pancreas extract were pooled and concentrated by ultrafiltration as indicated in Step No. A-8 above.

9. Antibodies against normal human plasma were removed from the concentrated solution by passage over a column (2.5 × 50 cm) of normal human plasma immobilized on Sepharose 4B. The column contained 0.114 ml of plasma per ml of Sepharose, and was prepared as follows:

250 ml of Sepharose 4B, which had been extensively washed with water, was suspended in 250 ml 0.1 M $Na_2CO_3$, $pH$ 11.0, and placed in an icebath. 30 g solid CNBr were added to the Sepharose 4B with stirring. The pH was monitored and maintained at 11.0 with the addition of 6 M NaOH for 30 minutes. The Sepharose was filtered on a Buchner funnel and washed exhaustively with 0.5 M $NaHCO_3$, pH 9.0, and added to a solution of 60 ml normal human serum in 140 ml of the same buffer. Stirring was maintained overnight at room temperature. The Sepharose-serum conjugate was filtered on a Buchner funnel and washed exhaustively with water and suspended in 300 ml of 0.1 M glycine in 0.5 M $NaHCO_3$, $pH$ 9.0 and stirred 2 hours. The Sepharose-serum conjugate was filtered and washed extensively with 0.1 M $Na_2HPO_4$, $pH$ 8.0; washed extensively with water; suspended in 0.095 M tris-acetate, 0.15 M NaCl, $pH$ 7.5, and packed into the column.

The column was eluted with 0.095 M tris-acetate, 0.15 M NaCl, $pH$ 7.5, at a flow rate of 18 ml/hour. Five ml fractions were collected.

10. The fractions were monitored as indicated in Step No. B-7 above.

11. Fractions with positive precipitin reactions with pancreas extract were pooled and concentrated as indicated in Step No. A-8 above.

12. The purified, concentrated antiserum was stored frozen or refrigerated until use.

EXAMPLE 5A

First Preparation of an Antigen Fraction from Normal Human Pancreas

In all of the above examples, the tissue extracts were monitored by absorbance and immunodiffusion with adsorbed antisera to antigens from the same organ which had been derived from prior preparations. A first preparation of an antigen fraction from a particular organ would have to differ in that such monitoring would not be possible. In the preparation of an antigen fraction from normal human pancreas, for example, Steps A-1 through A-5 of Example 5 would be followed, as described above, and then:

6. The fractions are monitored by absorbance at 280 nm, by immunodiffusion (in 2% agarose, 7.5% glycine, 1% sodium chloride, 0.1% $NaN_3$, $pH$ 7.1) with rabbit anti-whole human serum, and by disc electrophoresis on polyacrylamide gel columns as specified by Davis (B. J. Davis, Ann. N.Y. Acad. Sci. 121: 404, 1964).

7. A pool of fractions, designated fraction A, and corresponding to the last absorbance peak at 280 nm, is made based on lack of positive precipitin reactions with the anti-whole human serum.

8. The pool is concentrated approximately 5-fold by ultrafiltration (Amicon ultrafiltration cell employing PM-10 membrane).

9. The concentrate is dialyzed against water and lyophilized.

The lyophilized powder is then used for immunization of New Zealand white rabbits as indicated in Section B of Example 5. Antisera, obtained within two months after beginning immunization, are absorbed extensively with normal human plasma as indicated in Step B-2 of Example 5, and used to monitor subsequent antigen purifications as indicated in Steps A-1 through A-13 of Example 5.

In the Examples described above, immunogens have been injected into the host animals after fractionation of the tissue extracts by means of one or more fractionation techniques. It is to be understood, however, that in the fractionation techniques described, other fractions are obtained which contain other immunogens or groups of immunogens; and that such other fractions may also be used to inject host animals and to thereby produce different antibodies which may also be of diagnostic value.

Further, the separation techniques may be eliminated or abbreviated so that the material injected into the host animals comprises an immunogen mixture of broader spectrum. Or conversely, further separation techniques may be employed so that the material injected into the host animal comprises a single immunogen or a narrow spectrum mixture. In general, the degree of separation of the fractions of tissue extract before injection into the host animal is dependent on the concentration and immunogenicity of the immunogens for which antibodies are to be developed.

Another factor to be considered in determining the degree of separation of the tissue extract to be injected is the difficulty of isolating antibody fractions from the serum of the host animal where it has developed an immune response to a broad spectrum injection of immunogens.

The antisera fractions derived from the different organ tissues, as described above, are utilized in the testing of serum samples from patients suspected of having abnormal conditions in a particular organ. For a patient having a possible abnormal liver condition, for example, a serum sample may be tested for the presence of normal liver antigen fraction C by immunodiffusion (in 2% agarose, 7.5% glycine, 1% NaCl, 0.1% $NaN_3$, $pH$ 7.1) against the antiserum of Example 1. When precipitin lines are observed, the presence of the normal liver antigen in the serum is established, indicating an abnormal liver condition. Particularly strong positive precipitin reactions include severe malfunction. Normal sera do not show precipitin reactions with the antiserum of Example 1.

In the Examples described above, specific techniques have been described for the preparation of the antigen fractions, for the preparation of the purified antisera and for the assay of immunological reactions. It is to be understood, however, that the principles of this invention may be put into effect with other techniques.

In the purification of the antigen fractions, for example, Sephadex gel filtration material in sizes other than those disclosed in the Examples may be used. Alternatively, polyacrylamides or agarose materials may be used for the gel filtration chromatography.

For the ion exchange chromatography steps in the preparation of the antigen fractions, QAE-Sephadex has been used in the Examples. DEAE-Sephadex (diethylaminoethyl-Sephadex) materials may also be used. Additionally, ion exchange materials having diethylamino, or other anion exchange groups on matrices of cellulose, polyacrylamide resins, or agarose can be used.

In the above Examples, extensive use has been made of tris-acetate buffered sodium chloride solutions for the extraction and purification procedures. Other suitable buffers include imidazole, phosphates and glycine, and other suitable salts include potassium chloride and lithium chloride used in solutions at appropriate pH and ionic strength.

In the preparation of antisera, as described in the Examples, the New Zealand white rabbits used as the host animals were injected intramuscularly. Other modes of injection may be used, if desired, including subcutaneous, introperitoneal or intravenous injections.

The purification of the gamma globulin fraction in the preparation of organ-specific antisera has included ammonium sulfate precipitation and gel filtration chromatography. Alternatives for producing a purified gamma globulin fraction include the use of precipitins, disodium sulfate, ethanol, and polyethylene glycol. Alternatively, gel filtration chromatography or ion exchange may be used as the sole purification procedure and may utilize the media disclosed above for these steps.

Throughout the Examples, extensive use has been made of adsorbents immobilized on Sepharose. Alternatives for solid phase adsorption include the use of polymerized antigens prepared with the aid of materials such as glutaraldehyde, chromium chloride, and ethyl chloroformate, with or without the use of added carrier proteins. Matrices which may be used in place of Sepharose include other agarose preparations, cellulose and cellulose derivatives, and polyacrylamides and polyacrylamide derivatives.

For the in vitro assay of immunological reactions to identify the presence of organ-specific antigens in the sera of patients a number of techniques are available. Among the suitable techniques are those generally designated as immunodiffusion, immunoelectrophoresis and latex agglutination. These techniques are known to those skilled in the art. Immunodiffusion techniques are described, for example, in Williams and Chase "Methods in Immunology and Immunochemistry", Vol. III, pp. 118–145 (Academic Press, N.Y. — 1971); immunoelectrophoresis is described in the same text at pages 234–294.

Alternatively, in vitro assay may be performed by immuno-precipitation in non-supported liquid media. The precipitating antibody, when used at an appropriate relative concentration to the antigen, results in co-precipitation with that antigen, the quantity of precipitate being used to quantitate the antigen or the antibody. Assay of the precipitate can be made by measurement of turbidity (light scattering) or by measurement of protein or protein nitrogen.

Another alternative technique for in vitro assay of organ-specific antigen utilizes immuno-precipitation in supported media. In one form of this technique, known as the "radial diffusion" technique, or the "Mancini" technique, either the antigen or the antibody is incorporated in the support medium itself. Other examples of precipitation in supported systems include rocket immunoelectrophoresis and counterelectrophoresis which employ electric current to hasten the diffusion process, producing observable reactions in minutes instead of hours. The radial diffusion technique is described in Williams and Chase "Methods in Immunology and Immunochemistry," Vol. III, pp. 213–224, and in Mancini et al. "Immunochemistry," Vol. 2, pp. 235–254 (1965).

The in vitro assay of organ-specific antigens may also be accomplished by agglutination procedures in which microscopic particles are coated with antigens and then used to detect antibodies by agglutination when the two are mixed in appropriate relative concentrations. Conversely, the microscopic particles can be coated with antibodies and used to detect antigens. Suitable microscopic particles include red blood cells, micron-size latex particles and polyacrylamides and coating is accomplished by simple absorption procedures, or by the use of chemical coupling agents. Suitable agglutination procedures are described in Chapters 18 and 19 of "Methods in Immunology", Second Edition (1970), by Dan H. Campbell, Justine S. Garvey, Natalie E. Cremer and Dieter H. Sussdorf.

Complement fixation techniques may also be used to assay organ-specific antigens in sera. Complement fixation techniques are described in Chapters 21 and 22 of "Methods in Immunology," cited above.

The assay of organ-specific antigens may also be carried out by techniques utilizing labeled antibodies. Antibodies can be tagged with markers, such as fluorescent organic materials, enzymes, or radioactive atoms which can be employed to quantitate the antibody level. Assessment of the antibody-antigen reaction can be made employing such markers after separation of free antibodies from antibodies bound to antigen; and the separation may be achieved by the use of precipitins or by the use of gel filtration media, as described above.

The assay of organ specific antigens may also be carried out by techniques utilizing labeled antigens (radioimmunoassay). Antigens isolated and purified from human organs can be labeled with radioactive atoms and retain their immune reactivity. In a balanced ratio of radioactive antigen and antibody, addition of unlabeled antigen (in the form of either a standard control or physiological fluid specimen) will disturb the ratio, effecting decreased binding of radioactive antigen to antibody. This decreased binding is a manifestation of the presence of the antigen in question.

The nature of the host animals used to produce antibodies may also be varied. In addition to goats and rabbits, mentioned above, other suitable host animals include horses, sheep, rats, guinea pigs and dogs. Primates, such as rhesus monkeys, are not among the preferred species as host animals because they frequently have some of the same immunogens in their organs as do humans. In fact, for some immunogens, primates may serve as an alternate source where the supply of human tissue is limited.

In the above description, the body fluid tested for the presence of a particular antigen has been described as the blood of a patient; and in most cases a diagnosis in accordance with this invention will be carried out on an extract of blood, or a fraction thereof. It is to be understood, however, that antigens can also be detected in other body fluids, or extracts or fractions thereof, including spinal fluid, urine and sputum.

Other variations and modifications will be apparent to those skilled in the art.

What is claimed is:

1. A method of diagnosing a patent for an abnormal condition of a specific organ which comprises taking a sample of blood from said patient, adding to a soluble fraction of said blood a diagnostic material with respect to said specific organ and measuring any reaction product resulting from said addition, said diagnostic material comprising antibodies to at least one antigen normally present in the tissue of said specific organ of a healthy human and substantially free of any antibodies to all antigens present in the blood of a healthy human.

2. A method of diagnosing a patient for an abnormal liver condition which comprises taking a sample of blood from said patient, adding to a soluble fraction of said blood a diagnostic material and measuring any reaction product resulting from said addition, said diagnostic material comprising antibodies to at least one antigen normally present in the liver tissue of a healthy human, no portion of said diagnostic material being precipitable by any antigen normally present in the blood of a healthy human.

3. A method of diagnosing a patient for an abnormal kidney condition which comprises taking a sample of blood from said patient, adding to a soluble fraction of said blood a diagnostic material and measuring any reaction product resulting from said addition, said diagnostic material comprising antibodies to at least one antigen normally present in the kidney tissue of a healthy human, no portion of said diagnostic material being precipitable by any antigen normally present in the blood of a healthy human.

4. A method of diagnosing a patient for an abnormal heart condition which comprises taking a sample of blood from said patient, adding to a soluble fraction of said blood a diagnostic material and measuring any reaction product resulting from said addition, said diagnostic material comprising antibodies to at least one antigen normally present in the heart tissue of a healthy human, no portion of said diagnostic material being precipitable by any antigen normally present in the blood of a healthy human.

5. A method of diagnosing a patient for an abnormal skeletal muscle condition which comprises taking a sample of blood from said patient, adding to a soluble fraction of said blood a diagnostic material and measuring any reaction product resulting from said addition, said diagnostic material comprising antibodies to at least one antigen normally present in the skeletal muscle tissue of a healthy human, no portion of said diagnostic material being precipitable by any antigen normally present in the blood of a healthy human.

6. A method of diagnosing a patient for an abnormal pancreas condition which comprises taking a sample of blood from said patient, adding to a soluble fraction of said blood a diagnostic material and measuring any reaction product resulting from said addition, said diagnostic material comprising antibodies to at least one antigen normally present in the pancreas tissue of a healthy human, no portion of said diagnostic material being precipitable by any antigen normally present in the blood of a healthy human.

7. The method of claim 1, wherein any reaction product resulting from said addition is detected by an immunodiffusion technique.

8. The method of claim 1, wherein any reaction product resulting from said addition is detected by an immunoelectrophoresis technique.

9. The method of claim 1, wherein any reaction product resulting from said addition is detected by an agglutination technique.

10. The method of claim 1, wherein any reaction product resulting from said addition is detected by a complement fixation technique.

11. The method of claim 1 wherein any reaction product resulting from said addition is detected by a technique utilizing antibodies labeled with a marker selected from the group consisting of fluorescent organic materials, enzymes and radioactive atoms.

12. The method of claim 1 wherein any reaction product resulting from said addition is detected by a method utilizing antigens labeled with a marker selected from the group consisting of fluorescent organic materials, enzymes and radioactive atoms.

* * * * *